(12) United States Patent
Holm

(10) Patent No.: US 6,540,716 B1
(45) Date of Patent: Apr. 1, 2003

(54) DIRECTIONAL ENDOSCOPIC DELIVERY OF MATERIAL

(75) Inventor: Niels Erik Holm, Birkerød (DK)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/306,039

(22) Filed: May 6, 1999

Related U.S. Application Data

(60) Provisional application No. 60/084,460, filed on May 6, 1998.

(51) Int. Cl.$^7$ ............................................... A61M 31/00
(52) U.S. Cl. .................................................... 604/93.01
(58) Field of Search ........................... 604/93.01, 94.01, 604/95.01, 95.02, 164.01, 164.02, 264, 27, 39, 523; 606/231

(56) References Cited

U.S. PATENT DOCUMENTS

| | | | | |
|---|---|---|---|---|
| 4,808,157 A | * | 2/1989 | Coombs | |
| 5,242,449 A | | 9/1993 | Zaleski | ..................... 606/107 |
| 5,354,279 A | * | 10/1994 | Hofling | |
| 5,626,564 A | * | 5/1997 | Zhan et al. | ................... 604/164 |
| 5,658,251 A | * | 8/1997 | Ressemann et al. | ......... 604/102 |
| 5,750,657 A | * | 5/1998 | Edwardson et al. | |
| 5,814,066 A | | 9/1998 | Spotnitz | ..................... 606/214 |
| 5,876,410 A | * | 3/1999 | Petillo | |
| 6,162,202 A | * | 12/2000 | Sicurelli et al. | |

* cited by examiner

Primary Examiner—Anhtuan T. Nguyen
Assistant Examiner—Ann Y Lam
(74) Attorney, Agent, or Firm—John M. Kilcoyne

(57) ABSTRACT

In accordance with the present invention a directional application system for applying one or more components to a desired internal site in a human or animal within a range of angular directions is disclosed. The present system comprises a source of the components; means for fluid communication integral at a first end with the source of components and at a second end with a directional nozzle; and a directional nozzle comprising an inner tube of resilient material integral at a first end with the second end of the fluid communication means and having a nozzle at a second end, the second end being bent to the maximum angle within the desired range of directions; and an outer tube of a material more rigid than the inner tube and having an opening at one end to allow the inner tube to slidably project through the opening, whereby the amount of projection of the bent end of the inner tubing through the opening determines the angular direction of the nozzle.

7 Claims, 2 Drawing Sheets

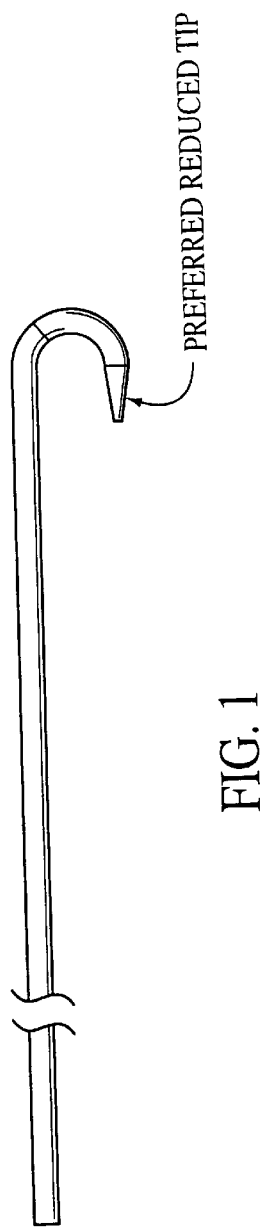
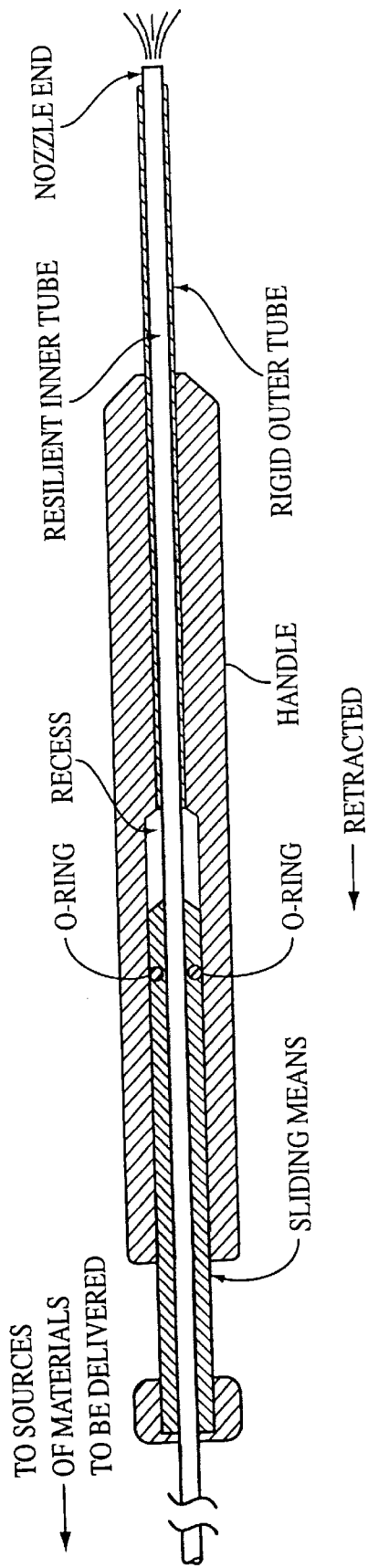

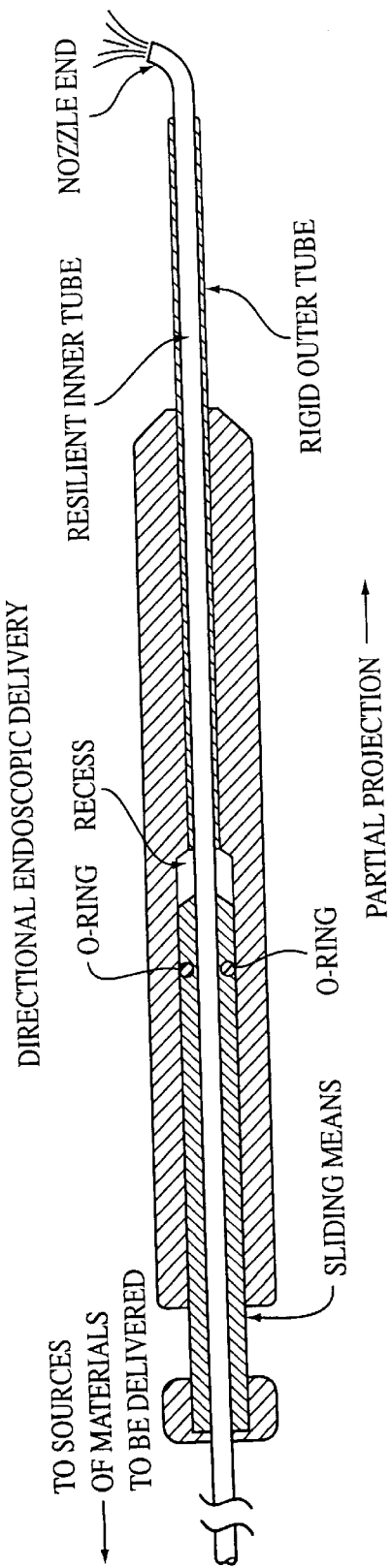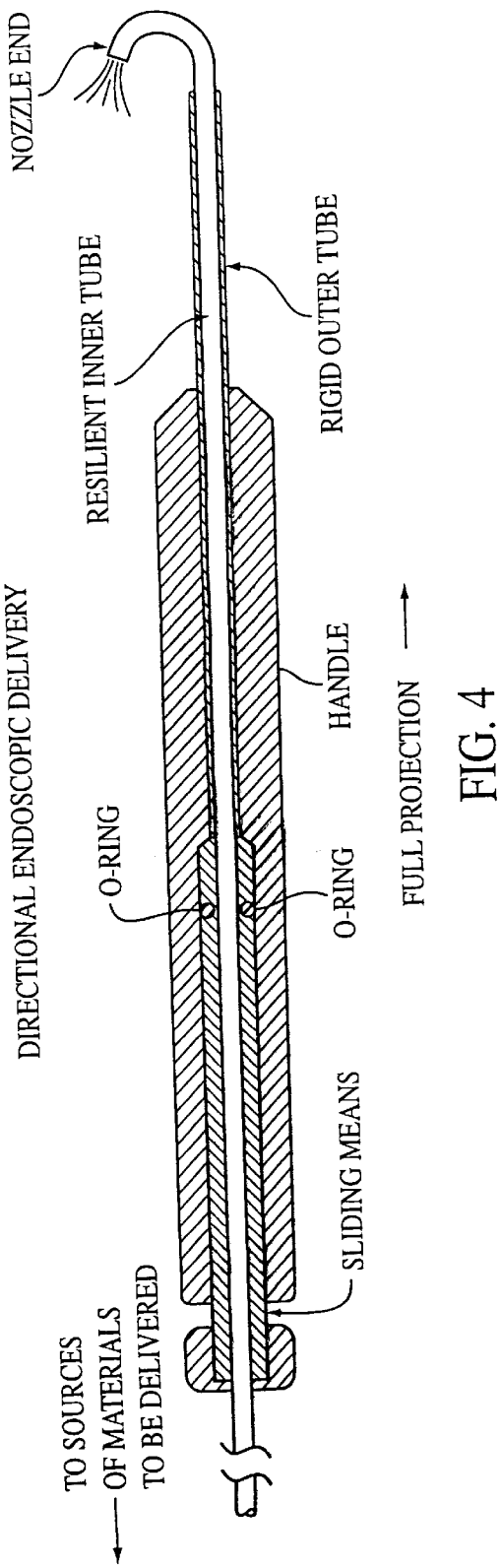

DIRECTIONAL ENDOSCOPIC DELIVERY OF MATERIAL

This application claims the benefit of Provisional Application No. 60/084,460 filed May, 6, 1998.

FIELD OF THE INVENTION

This invention relates to an applicator for the directional delivery of one or more materials to a desired internal site in a human or animal.

SUMMARY OF THE INVENTION

In accordance with the present invention a directional application system for applying one or more components to a desired internal site in a human or animal within a range of angular directions is disclosed. The present system comprises a source of the components; means for fluid communication integral at a first end with the source of components and at a second end with a directional nozzle; and a directional nozzle comprising an inner tube of resilient material integral at a first end with the second end of the fluid communication means and having a nozzle at a second end, the second end being bent to the maximum angle within the desired range of directions; and an outer tube of a material more rigid than the inner tube and having an opening at one end to allow the inner tube to slidably project through the opening, whereby the amount of projection of the bent end of the inner tubing through the opening determines the angular direction of the nozzle.

BRIEF DESCRIPTION OF THE DRAWINGS

FIG. 1 shows a section of resilient tube with the bent or curved nozzle end.

FIGS. 2–4 illustrate the different range of angular delivery possible depending upon the extent to which the resilient tube is projected out of or retracted into the second end of the rigid tube. Sliding means (or projecting/retracting means) can be provided at or near the first end of the rigid tube.

DETAILED DESCRIPTION OF PREFERRED EMBODIMENTS

Thus, the device of the present invention may be used to deliver materials endoscopically, i.e., via a body opening or duct to an organ, or through a surgical opening typically fitted with a trocar, e.g., laparoscopically or thorascopically, that is, into the abdominal or thoracic cavity. The invention comprises a directional dispensing or delivery device comprising an inner tube of a resilient material integral at a first end with a source or sources of the one or more materials to be delivered and having a nozzle at a second end. The second or nozzle end of the resilient material is bent or curved to the maximum angle within a desired range of angular directions for delivery of the materials. The inner tube is positioned slidably within an outer tube of a more rigid material such that the user can hold a first end of the rigid outer tube (which may be formed into a convenient handle) and such that the second end of the resilient tube can extend out of an opening at a second end of the rigid tube. The second end of the more rigid tube is positioned in the vicinity of the site to receive the desired materials, e.g., through the trocar. Means are provided to slide the resilient tube within the rigid tube so as to vary the length of the resilient tube projecting beyond the second end of the rigid tube. In doing this, the bent or curved nozzle (second) end of the resilient tube will assume, or be positioned at, varying angles to deliver or dispense the materials to a desired internal location.

The device and method of the present invention can be used for the endoscopic, laparoscopic or thorascopic delivery of any materials. They are conveniently employed to deliver components, e.g., liquid components, to a surgical site to form or deposit a polymer, e.g., a biopolymer. The present invention is particularly useful in the delivery of fibrin sealant components. Accordingly, the resilient inner tube may comprise separate tubes or one tube with multiple discrete channels to deliver a fibrinogen component and a component capable of converting fibrinogen to a fibrin polymer (sealant). Such a component is thrombin or another enzyme which catalyzes the cleavage of fibrinopeptides A and/or B from fibrinogen. According to U.S. Pat. No. 5,739,288 the fibrin sealant forming components (which are delivered in discrete tubes or channels) may also be a fibrin monomer component (which can be fibrin I, fibrin II or des ββ fibrin) and a component which will polymerize the fibrin component to form the sealant. In the case where the fibrin component is at low pH, i.e., pH4, the second component can be, for example, a pH10 buffer which facilitates the fibrin polymerization. The inner tube can be of a plastic material which can be bent or curved and which will strive to retain such a bend or curve. That is, the material of the inner tube needs to have some "memory" such that if it is initially bent or deformed to a desired maximum angle by known means, it will substantially return to that angle after being forced straight. Polyethylene multilumen tubing such as low density polyethylene tubing commercially available from the Putnam Company is suitable. Those multilumen tubings are preferably (each lumen) below about 500 microns in diameter, i.e., more preferably at or below 300 microns in diameter and most preferably the tubing has a reduced diameter portion such as described in WO 98/20931, incorporated herein by reference, such that the lumen diameters are about 120–150 microns in diameter. This involves heating and drawing the end of the tubing to produce a reduced diameter.

The resilient inner tube is in fluid communication directly or indirectly with sources of the components to be delivered. By indirectly is meant that the resilient tubing is in fact connected to a separate tubing or conduit which is, in turn, connected to the sources. Preferably the source of components are at a remote location and connected by tubing. This means that the user does not have to hold the sources of components in his/her hand and greater ease of use is provided. This is disclosed in WO 98/20931 and WO 97/20585 incorporated herein by reference. As mentioned in those patents, the sources of components are in a remote location as part of a mechanical or electromechanical drive unit to deliver the components from the sources to, and out the nozzle of, the present device. Delivery of the components from the sources, through the means for fluid communication and out of the directional nozzle, can be accomplished using a foot pedal which signals the drive unit. Alternatively, the present device may incorporate a handle for the user which may further include an actuator, button or trigger to actuate dispensing of the components.

Of course, the device of the present invention can be incorporated onto the delivery end of any medical component applicator, such as double barreled syringes, known in the art to apply fibrin sealants.

The more rigid outer tubing can be any material more rigid than the resilient inner tube. For example, medical grade plastics can be used and these are well known in the art. Examples include polypropylene or polycarbonate but can be any plastic so long as the outer tube is sufficiently rigid so that the inner bent resilient tube is "straightened" when drawn back into the outer tube. The outer tube can also be metal, e.g., stainless steel or other metal useful for internal medical devices.

The dimensions of the outer tube are adapted for their intended purpose. For endoscopic use the outer tube needs to be comparable to other endoscopic tubing for insertion into canals, e.g., esophagus, colon, etc., or into other body apertures or cavities. The laparoscopic use the outer tube needs to fit through a trocar. In practice, generally, the outer tube (with the inner tube withdrawn as in FIG. 2) is inserted into the area where component delivery is desired. Thereafter, the inner tube is extended sufficiently to provide the desired angular directional spray or delivery of components as shown in FIGS. 3 and 4. This can be used in conjunction with known endoscopic or laparoscopic cameras or optical equipment to observe/confirm the procedure.

As can be seen from FIGS. 2–4, in a preferred embodiment the present device includes a handle which can be a hollow tube-like part, cylindrical or otherwise. The rigid outer tube extends from a first end of the handle as shown in the figures. A means for sliding (or extending and withdrawing) the resilient inner tube within the outer tube is also a rigid material which is secured to the resilient tube, for example, by O-rings or other convenient fastening means. The means for sliding is adapted to slide in and out of a recess within a second end of the handle. This provides that when the means for sliding is slid in or out of the recess of the handle, the nozzle end of the resilient tube will extend or withdraw from the rigid outer tube as shown.

The present device is extremely useful in any endoscopic, laparoscopic, thorascopic or similar procedure where directional angular applications of components, e.g., fibrin sealant components, is required. It can be used in nearly all "minimally" invasive procedures and provides a great benefit by providing a comfort level to the surgeon, regarding fluid and air leakage, which is comparable to that realized in standard open surgical procedures.

A particular advantage is realized in thorascopic surgery especially video-assisted thorascopic surgery (VATS). For example, spontaneous pneumothorax (collapsed lung) is extremely difficult to treat due to the aperture, surgical cut or resection lines in the lung which have caused the collapse. Staples and/or sutures do not adequately seal air leak to reinflate the lung. Using standard, minimally invasive thorascopic procedures, the compromised lung is resealed using staples and/or sutures and the device of the present invention is utilized to apply fibrin sealant over the resection lines and staple lines. The ports used can be standard thorascopic ports of 10–16 mm and the application of sealant is preferably direct thorascopic supervision (VATS). Thereafter, the lung can be reinflated.

What is claimed is:

1. A directional application device for insertion of a directional spray nozzle into an internal cavity of a human or animal and applying therethrough one or more components to a desired internal site of a human or animal within a desired range of angular directions, the system comprising (a) a source of the components;
   (b) means for fluid communication integral at a first means end with the source of one or more components and at a second means end with the directional nozzle; and
   (c) the directional spray nozzle comprising
      (i) an inner tube of resilient material, the inner tube integral at a first tube end with the second means end and having a nozzle member at a second tube end, the second end being bent to the maximum angle within the desired range of directions, the second end being adapted to avoid piercing tissue in the internal cavity, the inner tube slidably movable within an outer tube, and wherein the inner tube is a multilumen tubing with discrete lumen for two or more components; and
      (ii) the outer tube of a material more rigid than the inner tube and having an opening at one end to allow the inner tube to slidably project through the opening, whereby the amount of projection of the bent end of the inner tubing through the opening determines the angular direction of the spray nozzle;

wherein the one or more components form a fibrin sealant.

2. The application device of claim 1 wherein the components comprise a fibrinogen component, carried in one lumen, and a second component, carried in a second lumen, including an enzyme which catalyzes the cleavage of fibrinopeptides A and/or B from fibrinogen.

3. The application device of claim 1 wherein the components comprise a fibrin monomer component carried in one lumen, and a second component for polymerizing the fibrin monomer carried in a second lumen.

4. The application device of claim 1 wherein the lumen are about 500 microns or less in diameter.

5. The application device of claim 1 wherein the nozzle end of the tubing is of a reduced diameter.

6. The application device of claim 1 wherein the lumen are about 150 microns or less in diameter.

7. A method for the treatment of spontaneous pneumothorax comprising (a) stapling or suturing an aperture or defect in a lung;
   (b) using the application device of claim 1 to apply a fibrin sealant to the staple line or suture line; and
   (c) reinflating the lung.

* * * * *